United States Patent [19]
Shore et al.

[11] Patent Number: 5,318,775
[45] Date of Patent: * Jun. 7, 1994

[54] SILICONE BASED COSMETIC PRODUCT

[75] Inventors: Kathleen M. Shore, Irving; Carlene C. Gregg, Dallas, both of Tex.

[73] Assignee: Mary Kay Cosmetics, Inc., Dallas, Tex.

[*] Notice: The portion of the term of this patent subsequent to Apr. 4, 2009 has been disclaimed.

[21] Appl. No.: 784,576

[22] Filed: Oct. 29, 1991

Related U.S. Application Data

[63] Continuation of Ser. No. 553,646, Jul. 18, 1990, Pat. No. 5,085,855.

[51] Int. Cl.⁵ .................. A61K 7/025; A61K 7/021
[52] U.S. Cl. ........................... 424/64; 424/63; 424/401
[58] Field of Search ............... 424/401, 64, 63; 514/887

[56] References Cited

U.S. PATENT DOCUMENTS

| | | | |
|---|---|---|---|
| 3,086,914 | 4/1963 | Soloway | 424/64 |
| 3,649,321 | 3/1972 | Durrant et al. | 106/443 |
| 3,864,140 | 2/1975 | Ferrigno | 106/462 |
| 3,947,571 | 3/1976 | Murphy et al. | 424/64 |
| 4,061,503 | 12/1977 | Berger et al. | 106/445 |
| 4,126,679 | 11/1978 | Davy et al. | 424/66 |
| 4,169,912 | 10/1979 | Schonafinger et al. | 428/145 |
| 4,291,018 | 9/1981 | Oeda et al. | 424/64 |
| 4,342,742 | 8/1982 | Sebag et al. | 424/59 |
| 4,344,799 | 8/1982 | Kohler et al. | 106/443 |
| 4,355,046 | 10/1982 | Suess | 514/772 |
| 4,367,220 | 1/1983 | Boulogne et al. | 424/64 |
| 4,390,524 | 6/1983 | Nasuno et al. | 424/63 |
| 4,423,032 | 12/1983 | Abe et al. | 424/70 |
| 4,492,686 | 1/1985 | Guillon et al. | 424/61 |
| 4,578,266 | 3/1986 | Tietjen et al. | 424/63 |
| 4,699,780 | 10/1987 | Jennings et al. | 424/60 |
| 4,795,631 | 1/1989 | Sheehan | 424/64 |
| 4,917,891 | 4/1990 | Kaufmann et al. | 424/63 |
| 4,935,228 | 6/1990 | Finkenaur et al. | 424/64 |
| 4,960,592 | 10/1990 | Hagen et al. | 424/537 |
| 5,066,485 | 11/1991 | Brieva et al. | 424/63 |
| 5,085,855 | 2/1992 | Shore | 424/64 |

Primary Examiner—Thurman K. Page
Assistant Examiner—Sally Gardner
Attorney, Agent, or Firm—Michael A. O'Neil

[57] ABSTRACT

Cosmetic formulations comprising mixtures of a polysiloxane having a viscosity at 25° C. of from about 500 centistokes to about 1500 centistokes, cosmetic grade lanolin oil, lanolin wax, a gelling agent, hydrocarbon-derived polymers such as polybutene or ethylene vinyl acetate, or mixtures thereof, and a dry color mix are disclosed. The dry color mix may comprise an inorganic pigment, mixtures of inorganic pigments or a mixture of inorganic pigments and a pearling agents.

5 Claims, No Drawings

SILICONE BASED COSMETIC PRODUCT

This is a continuation of application Ser. No. 07/553,646 filed Jul. 18, 1990, now U.S. Pat. No. 5,085,855.

TECHNICAL FIELD

This invention relates to a silicone based cosmetic product and more specifically to an improved lip color having a creamy consistency with improved adhesion and wearability characteristics.

BACKGROUND OF THE INVENTION

The use of various materials to stain, enhance or change the natural color of an individual's lips has been known since ancient times. In modern times, lip color change or enhancement is accomplished primarily through the use of pigments and coloring agents incorporated into a hard waxy material. The waxy material/coloring agent combination is typically made available in a stick form and is known in common parlance as lipstick. Although widely used, conventional lipsticks have a number of drawbacks. Conventional lipsticks can be difficult to apply due to their hard waxy nature and have limited wearability, primarily due to the fact that most lipsticks contain a relatively small percentage of pigment. Thus, conventional lipsticks must be reapplied at frequent intervals.

The use of dry powdered lip colors to enhance wearability over that of conventional lipsticks is also known. However, the use of powdered lip color can be inconvenient and time consuming. Moreover, while the use of powdered lip color may enhance wearability over lipsticks to some extent, powdered lip color tends to dry the wearer's lips and to undesirably enhance the appearance of wrinkles.

Cosmetic formulations incorporating silicones (organosiloxanes) have been proposed. Examples of such formulations are disclosed in the following U.S. Pat. Nos.: 4,699,780 issued Oct. 13, 1987 to Jennings et al.; 4,578,266 issued Mar. 25, 1986 to Tietjen et al.; 4,390,524 issued Jun. 28, 1983 to Nasuno et al.; and, 4,355,046 issued Oct. 19, 1982 to Suess. The foregoing references do not, however, teach the unique formulation of the present invention which provides an improved lip color with superior wearability.

SUMMARY OF THE INVENTION

The present invention provides a formulation for a lip color possessing superior wearability properties, the formulation comprising:

from about 10% to about 35% of a polysiloxane having a viscosity at 25° C. of from about 500 centistokes to about 1500 centistokes;

from about 10% to about 35% of a cosmetic grade lanolin oil having an acid value $\leq 2.0$, a saponification number from about 100 to about 120 and an iodine number from about 18 to about 40;

from about 5% to about 15% of a lanolin wax having an iodine number from about 18 to about 36, a hydroxyl number from about 20 to about 35, a saponification number from about 90 to about 110 and a melting point between about 45 to about 55° C.;

from about 10% to about 30% of a hydrocarbon derived polymer such as polybutene or ethylene vinyl acetate or a mixture thereof;

from about 10% to about 20% of a gelling agent; and, from about 15% to about 45% of a dry color mix. The composition may optionally contain additives such as stabilizers, perfumes, sun screens, antioxidants, preservatives and mixtures thereof. All percentages referred to herein are by weight unless otherwise noted.

DETAILED DESCRIPTION

The term silicone as used herein refers to organosiloxane polymers based on a structure consisting of alternating silicon and oxygen atoms with various organic radicals attached to the silicon:

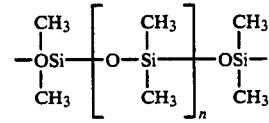

One such siloxane is dimethicone, a mixture of fully methylated linear siloxane polymers end blocked with trimethylsiloxy units.

Siloxane polymers may comprise liquids, semisolids, or solids depending upon molecular weight, and degree of polymerization. The siloxane polymers suitable for use in connection with the present invention are those polymers wherein the repeating unit n is such that the polymer comprises a liquid with a viscosity between about 500 centistokes and about 1500 centistokes. Siloxane polymers suitable for use in connection with the present invention include selected Dow Corning 200 Fluid Series available from Dow Corning Corporation, Midland, Mich. It is, however, contemplated that other commercially available polysiloxanes having the requisite physical properties will be suitable for use in connection with the formulation of the present invention.

Although polysiloxanes exhibit a number of desirable physical properties, such as extreme water repellency, low surface tension, high lubricity, non-greasy emollience and low skin penetration, the use of siloxanes in the formulation of lip glosses has been largely precluded by the basic incompatibility of the inorganic backbone of the siloxane polymer with the other organic components typically used in the formulation of lip glosses. This incompatibility typically results in phase separation of the organic components typically used in the formulation of lip glosses. The use of polysiloxanes in the formulation of lip glosses has also been limited by the difficulty of uniformly dispersing coloring agents such as pigments in polysiloxanes. It has, however, been discovered that a polysiloxane fluid having a viscosity between about 500 centistokes and about 1500 centistokes may be readily combined with a lanolin oil, a gelling agent, a lanolin wax and hydrocarbon-derived polymers such as polybutene and/or ethylene vinyl acetate copolymer or a mixture thereof, to form a mixture wherein a coloring agent such as an inorganic pigment or mixtures of inorganic pigments are readily dispersible, thereby providing a lip gloss with improved wearability.

Lanolin oils suitable for use in connection with the present invention have an acid value $\leq 2.0$, a saponification number from about 100 to about 120 and an iodine number from about 18 to about 40. Lanolin oils suitable for use in connection with the present invention are available from Croda Inc., New York, N.Y. under the trade designation Fluilan.

A lanolin wax is also used in the formulation of the present invention. Suitable lanolin waxes have an iodine number from about 18 to about 36, a hydroxyl value from about 20 to about 35, a saponification number from about 90 to about 110 and a melting point between about 45° C. and 55° C. To determine the hydroxyl value a sample is acylated in pyridine with acetic anhydride and back titrated with potassium hydroxide. The hydroxyl value is expressed as the mgs. of potassium hydroxide used per gram of sample. Lanolin waxes suitable for use in connection with the present invention are available from Henkel Corp., Morristown, N.J. under the trade designation Lanfrax-1777.

A gelling agent used in the formulation of the present invention is a lanolin oil/stearalkonium hectorite blend. The gelling agent is a translucent tacky gel with a viscosity from about 500,000 to about 1,100,000 cps. A gelling agent suitable for use in connection with the present invention is available from NL Industries, Houston, Tex. under the trade designation Bentone Gel LOI.

Hydrocarbon-derived polymers used in connection with the present invention include polybutene and ethylene vinyl acetate copolymer. Preferably the polybutene used in connection with the present invention is a clear viscous oily liquid having a density of from about 0.88 gm/cm$^3$ to about 0.90 gm/cm$^3$. A polybutene suitable for use in the formulation of the present invention is available from Amoco Chemicals Co., Chicago, Ill. under the trade designation Indopol H-100.

The ethylene vinyl acetate copolymer used in connection with the present invention is a granular or powdered wax preferably comprising from about 12% to about 16% vinyl acetate and has a needle penetration of from about 0.7 to about 1.1 mm as measured by ASTM D 1321-76 "Standard Test Method for Needle Penetration of Petroleum Waxes" (100 gms/5 sec @ 25° C., D5 needle), and a melting point from about 85° C. to about 95° C. An ethylene vinyl acetate copolymer suitable for use in connection with the present invention is available from Allied Chemical Corp., Morristown, N.J. under the trade designation PE-AC 400.

Minor amounts of other oils and waxes may be incorporated into the formulation of the present invention in order to achieve specific physical properties. Examples of such materials include high molecular weight fatty acids, alcohols and esters, candelilla, ozokerite, ceresine, carnauba, microcrystalline waxes and similar materials.

The formulation of the present invention may optionally contain antioxidants such as butylated hydroxyanisole (BHA) and antimicrobial agents such as methyl, ethyl, propyl and butyl esters of parahydroxybenzoic acid sold under the trade designation Paraben. Flavoring agents and perfumes may also be used in the formulation of the present invention in order to provide a pleasant flavor and odor.

The formulation of the present invention provides a medium or base blend wherein coloring agents such as pigments and mixtures of pigments may be uniformly dispersed at relatively high proportions, from about 20% to about 45% by weight. A wide variety of pigments and pearling agents are suitable for use in the compositions of the present invention. Such materials include D&C Red #6, D&C Red #7, D&C Red #27, FD&C Yellow #5, FD&C Blue #1, Soloron Silver, Timiron Super Violet, iron oxides, carmine, mica, titanium dioxide, talc and the like.

The invention will be further described with respect to the following examples; however, the scope of the invention is not to be limited thereby.

EXAMPLE 1

Referring now to Table 1 below, the indicated quantity of an ethylene vinyl acetate copolymer and a Dow Corning Series 200 silicone fluid having a viscosity at 25° C. of 500 centistokes was heated to between about 90° C. and about 95° C. and maintained at that temperature until the ethylene vinyl acetate was melted. The indicated quantity of a lanolin wax was then added and the batch was mixed until the lanolin wax was melted. The batch was then cooled to approximately 80° C. Lanolin oil along with a lanolin oil/stearalkonium hectorite gelling agent, the components of phases C and D, were then added to the batch. The batch was mixed until it achieved a uniform consistency at which time the components of phase E were added. The mixing was continued for a sufficient time to ensure that all the components were uniformly dispersed throughout the mixture.

TABLE 1

| Phase | Material | Grams | Weight % |
|---|---|---|---|
| | Base | | |
| A | Ethylene Vinyl Acetate | 150.20 | 7.51 |
| A | Silicone Fluid (500 cst) | 461.40 | 23.07 |
| B | Lanolin Wax | 171.20 | 8.56 |
| C | Lanolin Oil | 429.40 | 21.47 |
| D | Lan. Oil/Stearalkonium Hect. | 429.40 | 21.47 |
| E | Polybutene | 346.60 | 17.33 |
| E | Methylparaben | 2.60 | 0.13 |
| E | Butylparaben | 2.60 | 0.13 |
| E | Propylparaben | 2.60 | 0.13 |
| E | BHA | 1.40 | 0.07 |
| E | Fragrance | 2.60 | 0.13 |
| | | 2000.00 | 100.00 |

TABLE 2

| Material | Weight % |
|---|---|
| Dry Color Mix | |
| Talc, 100% | 58.69 |
| Cosmetic Yellow Iron oxide | 4.50 |
| Black Iron oxide | 1.05 |
| 50/50 Talc-Red #6 Blend | 12.05 |
| 50/50 Talc-Red #7 Blend | .21 |
| Titanium Dioxide | 18.00 |
| Tridecyl Neopentanoate | 5.50 |
| | 100.00 |

A dry color mix of the composition set forth in Table 2 above was homogenized with the base blend of Table 1 at rates of 25%, 35% and 45% by weight. In each case the dry color mix was readily and uniformly dispersed throughout the base.

EXAMPLE 2

Referring now to Table 3 below, the components of phases A-E were mixed in generally the same fashion as set forth in Example 1 except that a portion of the silicone fluid was added after the addition of the lanolin wax. Also, as indicated, the silicone fluid used in the composition of Table 3 had a viscosity of 1000 centistokes at 25° C. as opposed to the fluid used in Example 1, which had a viscosity of 500 centistokes. The dry color mix portion of the composition of Table 3 constitutes approximately 28% by weight of the composition. The dry color mix portion of the composition was readily and uniformly dispersed throughout the mixture.

TABLE 3

| Phase | Material | Grams | Weight % |
|---|---|---|---|
| A | Ethylene Vinyl Acetate | 24.50 | 5.04 |
| A | Silicone Fluid (1000 cst) | 38.60 | 7.93 |
| B | Lanolin Wax | 28.10 | 5.77 |
| C | Silicone Fluid (1000 cst) | 39.60 | 8.14 |
| D | Lanolin Oil | 70.10 | 14.42 |
| D | Lan. Oil/Stearalkonium hect. | 70.10 | 14.42 |
| E | Polybutene | 52.60 | 10.81 |
| E | Methylparaben | 0.68 | 0.14 |
| E | Butylparaben | 0.68 | 0.14 |
| E | Propylparaben | 0.68 | 0.14 |
| E | BHA | 0.19 | 0.04 |
| E | Lip Gloss Flavor | 0.68 | 0.14 |
| E | Red #7/Caster Oil blend | 1.90 | 0.41 |
| E | Yellow I.O./Castor Oil blend | 4.00 | 0.83 |
| E | TiO₂/Castor Oil blend | 15.60 | 3.21 |
| E | Blue #1/Castor Oil blend | 0.24 | 0.05 |
| E | Red #6/Castor Oil blend | 2.10 | 0.44 |
| F | Talc (Dry Color Mix) | 109.20 | 22.46 |
| F | TiO₂ (Dry Color Mix) | 12.20 | 2.51 |
| F | Red #7/Talc (Dry Color Mix) | 2.40 | 0.51 |
| F | Red I.O. (Dry Color Mix) | 8.80 | 1.82 |
| F | Yellow I.O. (Dry Color Mix) | 0.88 | 0.18 |
| F | Ultramarine Blue (Dry Color Mix) | 2.19 | 0.45 |
|   |   | 486.02 | 100.00 |

I.O. = Iron Oxide

COMPARATIVE EXAMPLE 3

Referring now to Table 4 below the components of phases A-F were blended in the indicated quantities in generally the same fashion as set forth Example 4 above. As indicated in Table 4, silicone fluids with two different viscosities were used. A Dow Corning Series 200 silicone fluid with a viscosity of 1000 centistokes at 25° C. was used with another Series 200 silicone fluid having a viscosity of 5000 centistokes in relative proportions so as to result in an equivalent silicone fluid viscosity of approximately 2000 centistokes. The base blend of Table 4 was blended with 15%, 25% and 35% by weight of the dry color mix of Table 2 above. The 15% dry color mix/85% base blend mixed with uniform dispersion of the color mix throughout the base. However, at the 25 and 35% levels of dry color mix the dry color mix did not blend well and the batch became too hot during the mixing process. At the 15% dry color mix level the pigment level provided marginal color in the product.

TABLE 4

| Phase | Material | Grams | Weight % |
|---|---|---|---|
| A | Ethylene Vinyl Acetate | 150.40 | 7.52 |
| B | Silicone Fluid (1000 CST) | 346.00 | 17.30 |
| C | Lanolin Wax | 171.20 | 8.56 |
| D | Silicone Fluid (5000 CST) | 115.20 | 5.76 |
| E | Lanolin Oil | 429.40 | 21.47 |
| E | Lan. Oil/Stearalkonium hect. | 429.40 | 21.47 |
| F | Polybutene | 346.60 | 17.33 |
| F | Methylparaben | 2.60 | 0.13 |
| F | Butylparaben | 2.60 | 0.13 |
| F | Propylparaben | 2.60 | 0.13 |
| F | BHA | 1.40 | 0.07 |
| F | Fragrance | 2.60 | 0.13 |
|   |   | 2000.00 | 100.00 |

COMPARATIVE EXAMPLE 4

The components of Table 5 below were blended together in the same fashion as set forth in Example 4 above. As indicated, a Dow Corning Series 200 silicone fluid having a viscosity of 350 centistokes at 25° C. was used in the base blend of Table 4. The base mixture was then blended with a dry color mix of the composition set forth in Table 6 below, at a rate of 25% by weight. The lip gloss of this example, however, proved unsatisfactory in so far as the mixture bled oil. Additionally, the mixture did not provide acceptably uniform coverage upon application.

TABLE 5

| Phase | Material | Grams | Weight % |
|---|---|---|---|
| A | Ethylene Vinyl Acetate | 100.80 | 6.72 |
| A | Silicone Fluid (350 CST) | 158.70 | 10.58 |
| B | Lanolin Wax | 115.35 | 7.69 |
| C | Silicone Fluid (350 CST) | 324.15 | 21.61 |
| D | Lanolin Oil | 288.45 | 19.23 |
| E | Lan. Oil/Stearalkonium Hect. | 288.45 | 19.23 |
| F | Polybutene | 216.15 | 14.41 |
| F | Methylparaben | 3.00 | 0.20 |
| F | BHA | 0.90 | 0.07 |
| F | Flavor | 0.27 | 0.02 |
|   |   | 1496.22 | 100.00 |

TABLE 6

| Material | Weight % |
|---|---|
| Talc | 80.41 |
| TiO₂ | 9.00 |
| Red #7 50/50 Talc blend | 1.83 |
| Red Iron Oxide | 6.51 |
| Ultramarine Blue | 1.60 |
| Yellow Iron Oxide | 0.65 |
|   | 100.00 |

EXAMPLE 5

Referring to Table 7 below, a composition of the present invention was manufactured on a commercial scale. The indicated quantity of lanolin oil was added to a clean sanitized main vessel and heated to from about 70° C. to about 75° C. A dry color mix of the composition of Table 2 was added to the lanolin and a high speed propeller-type mixer was used to blend the lanolin/dry color mix until a slurry was formed. The mixture was then homogenized for approximately 30 minutes using a conventional in-vessel cylindrical homogenizer. A Hegman pharmaceutical draw-down gauge was then used to check dispersion of the pigment. It is considered important to have a gauge reading of less than about 25 microns at this stage.

Ethylene vinyl acetate copolymer and Dow Corning Series 200 silicone fluid with viscosity of 1000 centistokes were added to a clean, sanitized auxiliary vessel. The ethylene vinyl acetate/silicone fluid mix was heated to approximately 95° C. and mixed until the ethylene vinyl acetate was completely melted. The lanolin wax was then added to the auxiliary vessel and mixing continued until the wax was completely melted. The mixture from the auxiliary vessel was then mixed with the lanolin oil/dry color mix in the main vessel.

The lanolin oil/stearalkonium hectorite gelling agent was then added to the batch and the temperature of the bath was allowed to drop to between about 70° C. and about 75° C. while the batch was homogenized for approximately 30 minutes. The E and F phase components were then added to the batch and mixing was continued for approximately 10 minutes. The batch was then homogenized for approximately 15 minutes and the phase G component was then mixed into the blend until dispersed. The dry color mix was readily and uniformly dispersed throughout the base. The resulting lip gloss provided consistent uniform coverage upon application and had excellent wearability characteristics.

TABLE 7

| Phase | Material | Kilograms | Weight % |
|---|---|---|---|
| A | Lanolin Oil | 249.55 | 16.10 |
| A | Dry Color Mix | 387.50 | 25.00 |
| B | Ethylene/Vinyl Acetate | 87.26 | 5.63 |
| B | Silicone Fluid(1000 CST) | 268.15 | 17.30 |
| C | Lanolin Wax | 99.51 | 6.42 |
| D | Gelling Agent | 249.55 | 16.10 |
| E | Methylparaben | 1.55 | 0.10 |
| E | Butylparaben | 1.55 | 0.10 |
| E | Propylparaben | 1.55 | 0.10 |
| F | Polybutene | 201.50 | 13.00 |
| F | BHA | 0.78 | 0.05 |
| G | Perfume Oil | 1.55 | 0.10 |
|   |   | 1550.00 | 100.00 |

While the present invention has been described in connection with the foregoing examples, it is to be understood and appreciated that various other changes, modifications and substitutions may be made without departing from the spirit and scope of the invention as claimed herein.

I claim:

1. A process for preparing a lip color formulation comprising:
mixing from about 15% to about 45% of a dry color mix with: (a) from about 10% to about 35% of a dimethicone siloxane having a viscosity at 25° C. of from about 500 centistokes to about 1500 centistokes; (b) from about 10% to about 35% lanolin oil having an acid value $\leq 2.0$, a saponification number from about 100 to about 120 and an iodine number from about 18 to about 40; (c) from about 5% to about 15% of a lanolin wax having a an iodine number from about 18 to about 36, a hydroxyl number from about 20 to about 35, a saponification number from about 90 to about 110, and a melting point from about 45° C. to about 55° C.; (d) from about 10% to about 20% of a lanolin oil/stearalkonium hectorite gelling agent; and (e) from about 10% to about 30% of hydrocarbon-derived polymers selected from the group comprising polybutenes and ethylene vinyl acetate copolymers.

2. The process of claim 1 wherein the dry color mix comprises an inorganic pigment.

3. The process of claim 1 wherein the dry color mix comprises a mixture of inorganic pigments.

4. The process of claim 1 wherein the dry color mix comprises a mixture of inorganic pigments and pearling agents.

5. A process for preparing a lip color formulation comprising:
mixing 15% to 45% of inorganic pigments with a base comprising: (a) 10% to 35% of a dimethicone siloxane having a viscosity at 25° C. of 500 centistokes to 1500 centistokes; (b) 10% to 35% of a lanolin oil having an acid value $\leq 2.0$, a saponification number from 100 to 120 and an iodine number from 18 to 40; (c) 5% to 15% of a lanolin wax having a an iodine number from 18 to 36, a hydroxyl number from 20 to 35, a saponification number from 90 to 110, and a melting point from 45° C. to 55° C.; (d) 10% to 20% of a lanolin oil/stearalkonium hectorite gelling agent; and (e) 10% to 30% of hydrocarbon-derived polymers selected from the group comprising polybutenes and ethylene vinyl acetate copolymers.

* * * * *